United States Patent
Sarlikiotis et al.

(10) Patent No.: US 6,284,287 B1
(45) Date of Patent: *Sep. 4, 2001

(54) PARTICULATE FORMULATION FOR ADMINISTRATION BY INHALATION

(75) Inventors: Werner Sarlikiotis, Frankfurt (DE); Anne De Boer, Drachten (NL)

(73) Assignee: Asta Medica AG, Dresden (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/765,928
(22) PCT Filed: Jun. 21, 1995
(86) PCT No.: PCT/EP95/02392
  § 371 Date: Apr. 2, 1997
  § 102(e) Date: Apr. 2, 1997
(87) PCT Pub. No.: WO96/02231
  PCT Pub. Date: Feb. 1, 1996

(30) Foreign Application Priority Data

Jul. 16, 1994 (DE) .................................. 44 25 255

(51) Int. Cl.⁷ ...................................................... A61K 9/14
(52) U.S. Cl. ........................................... 424/689; 424/46
(58) Field of Search ................................ 424/45, 46, 489

(56) References Cited

U.S. PATENT DOCUMENTS

| | | |
|---|---|---|
| 3,634,582 | 1/1972 | Hartley et al. . |
| 3,860,618 | 1/1975 | Hartley et al. . |
| 3,957,965 | 5/1976 | Hartley et al. . |
| 4,009,280 | 2/1977 | Macarthur et al. . |
| 4,161,516 | 7/1979 | Bell . |
| 4,199,578 | 4/1980 | Stevenson . |
| 4,409,237 | 10/1983 | Caims et al. . |
| 5,310,753 | 5/1994 | Englert et al. . |
| 5,376,386 | 12/1994 | Ganderton et al. . |
| 5,658,549 | * 8/1997 | Akehurst et al. . |

FOREIGN PATENT DOCUMENTS

| | | |
|---|---|---|
| 1112567 | 11/1981 | (CA) . |
| 2125685 | 6/1993 | (CA) . |
| 2115065 | 12/1993 | (CA) . |
| 2174767 | 5/1995 | (CA) . |
| 28 51 489 | 5/1979 | (DE) . |
| 0239798 | 7/1987 | (EP) . |
| 1381872 | 1/1975 | (GB) . |
| 1520247 | 8/1978 | (GB) . |
| 1520248 | 8/1978 | (GB) . |
| 1571629 | 7/1980 | (GB) . |
| 47829 | 9/1972 | (IL) . |
| 51233 | 9/1972 | (IL) . |
| 57956 | 9/1972 | (IL) . |
| 62744 | 2/1981 | (IL) . |
| 91/11179 | 8/1991 | (WO) . |
| 92/11016 | 7/1992 | (WO) . |
| 95/091616 | 4/1995 | (WO) . |
| 95/11666 | 5/1995 | (WO) . |

OTHER PUBLICATIONS

Köhler, D. (1993). Systemic Therapy With Aerosols. In: Morén et al. (eds.), Elsevier, pp. 303–319.*
Patton, J.S. and R.M. Platz. (1992). Route of Delivery: Case Studies. Advanced Drug Delivery Reviews, 8:179–196.*

* cited by examiner

*Primary Examiner*—Raj Bawa
(74) *Attorney, Agent, or Firm*—Pillsbury Winthrop LLP

(57) ABSTRACT

A pharmaceutical formulation for administration by inhalation, a micronized active compound or micronized active compound mixture with a mean particle size of 0.1 μm to 10 μm being applied to a pharmaceutically acceptable excipient having a mean particle size of 200 μm to 1000 μm without the use of binders.

16 Claims, No Drawings

PARTICULATE FORMULATION FOR ADMINISTRATION BY INHALATION

BACKGROUND OF THE INVENTION

1. Field of the Invention

The present invention relates to a pharmaceutical formulation for administration by inhalation, the micronized active compound or the micronized active compound mixture being applied to an excipient without binders being used.

2. Background Information

Active compounds which are administered by inhalation must penetrate deep into the lungs in order to show topical or alternatively systemic action. In order to achieve this, the particles of the active compound must have a diameter which does not exceed approximately 5 μm–10 μm. Additionally, the active compound or the active compound mixture is administered to the patient with the aid of a specially made device, an inhaler. The active compound here must first be either predosed, for example in capsules or blister packs, or stored in a relatively large amount in the inhaler in order then to be removed from a measuring device by the inhalation process of the patient and redispersed into the fine primary particles with a dispersing device, for example a fluidizing chamber, carried along with the breath and thus made available to the lungs.

On account of the particle size a high specific surface area of the particles and a distribution of forces resulting therefrom, the very fine-grained active compounds used for this purpose have very pronounced adhesive and cohesive properties, which in turn has the result that the processing of such powders regarding process technology runs into difficulties. Such process technology steps are the mixing of the active compounds in active compound mixtures, the storage and the transport of the powders, the filling of capsules, blister packs or inhalers, and the dosage of the therapeutic amounts.

The agglomeration processes customary in pharmacy, e.g. granulation, cannot be employed because the particles are so strongly bound to one another thereby that respirable active compound particles are no longer present or can no longer be generated. Additionally, at present most of the pharmaceutically customary auxiliaries cannot be used in pharmaceutical forms for inhalation, as the toxicological behavior of these substances on pulmonary administration is still largely unknown.

In order to solve the problems mentioned, it was proposed, for example, in EP 0 398 631 to grind the active compound down to a mean particle diameter of 5 μm to 10 μm and then either to mix it with a solid, pharmaceutically customary excipient, this having a mean particle diameter of 30 μm to 80 μm, or else to prepare round agglomerates of the active compound particles (so-called soft pellets), these disintegrating into the primary particles again during inhalation. A process for the preparation of such soft pellets is also described (GB 1,569,612 and GB 1,520,247). In this process, the moisture content of the active compound must be adjusted before the preparation of the soft pellets. The soft pellets can be filled into capsules as described, for example, in DE 25 35 258 and GB 1,520,247. In vitro experiments showed that on emptying these capsules with the aid of an inhaler at least 50% of the filled material was emptied.

However, these soft pellets, prepared according to the abovementioned procedures, have a dispersing rate (=proportion of the respirable active compound particles after emptying, relative to the amount dispensed in the capsule), which may still not be satisfactory.

With a volume flow of 60 1/min, dispersing rates of 13.8–29.5% of the nominal dose were found for available systems in the cascade impinger (four-stage liquid impinger).

In another process (DE 22 29 981), the active compound is mixed with a pharmaceutically utilizable, water-soluble excipient, this excipient having a particle size of 80 μm to 150 μm.

The disadvantage here is the poor flow properties of the formulation.

DE 41 40 689 describes inhalation powders which consist of a physiologically acceptable auxiliary having a mean particle size of about 20 μm and a second component auxiliary having smaller particles of approximately 10 μm particle size.

This mixture can be filled into capsules and is inhaled using apparatuses which are described in DE 33 45 722. Here too the poor flow properties are a disadvantage.

EP 258 356 describes microparticles for inhalation purposes, which consist of a conglomerate of auxiliaries, for example lactose, xylitol and mannitol of a size between 30 μm and 150 μm. A problem in this process is the relatively complex preparation path in order to prepare auxiliary conglomerates having a specific particle size.

SUMMARY OF THE INVENTION

DE 28 51 489 A1 describes a formulation consisting of beclomethasone dipropionate whose particles to 90% by weight are smaller than 10 μm and of a powder excipient which consists of particles having an effective size of 90% by weight less than 400 μm and of at least 50% by weight greater than 30 μm. In addition to the active compound beclomethasone dipropionate, this formulation can additionally contain a bronchodilator of preferably the same particle size as beclomethasone dipropionate.

Designated bronchodilators are orciprenaline, terbutaline or salbutamol. Conversion to a pharmaceutical preparation is carried out by simple mixing.

WO 91/11179 A1 describes the use of excipient materials such as lactose, polysaccharides and others. As described, these excipient materials have a particle size of 5.0–1000 μm and a surface roughness of less than 1.75. Simple mixing of the excipient material with a pharmaceutical active compound leads to the powder preparation.

The object is thus, for the purposes of inhalation, to develop a powder which is simple to prepare, requires no complicated in-process controls of the moisture content of the active compounds and/or auxiliaries and has a high degree of redispersion. Furthermore, the formulation should have satisfactory flow properties and be easily disintegrable into respirable particles in the inhaler. Under identical conditions, at least 40% should be redispersed.

It has now surprisingly been found that by suitable mixing of the active compound or of the active compound mixture with a pharmaceutically utilizable excipient which has a mean particle size of 200 μm to 1000 μm, preferably between 300 μm and 600 μm, and a roughness of more than 1.75, the active compound particles having a particle size of 0.01 μm to 10 μm adhere to the excipient particles and thereby almost round excipient particles coated with active compound result. In the case of the formulation according to the invention, treatment, for example additional purification processes, of the excipient material employed can be dispensed with.

The particles of the excipient are commercially available or can be obtained by fractionation (sieve) into a specific grain size or grain size range.

The determination of the particle size of the excipient particles was carried out by measurement of scanning electron microscope photographs and/or by sieve analysis. The determination of the particle size of the active compound particles was carried out by measurement of scanning electron microscope photographs and/or by laser diffraction spectrometry.

This powder formulation can be prepared simply and economically and has significantly better flow properties both in comparison to the untreated active compound powder and to the soft pellets. The results in Table 1 show this. A lower bed height means better flow properties of the formulation.

The more similar the bulk and compacted volumes are, the better the flow properties. However, even the emptying and subsequent redispersion is better in comparison to the previously known formulations (mixtures, soft pellets according to GB 1 569 612 or GB 1 520 247 or untreated active compound powder), i.e. the residues in the inhaler are lower and the yield of respirable particles is higher.

The formulation can contain various active compounds, for example analgesics, antiallergics, antibiotics, anticholinergics, antihistaminics, antiinflammatory substances, antipyretics, corticoids, steroids, antitussives, bronchodilators, diuretics, enzymes, cardiovascular substances, hormones, proteins and peptides. Examples of analgesics are codeine, diamorphine, dihydromorphine, ergotamine, fentanyl and morphine; examples of antiallergics are cromoglycic acid and nedocromil; examples of antibiotics are cephalosporins, fusafungin, neomycin, penicillins, pentamidine, streptomycin, sulfonamides and tetracyclines; examples of anticholinergics are atropine, atropine methonitrate, ipratropium bromide, oxitropium bromide and trospium chloride; examples of antihistaminics are azelastine, flezelastine and methapyrilene; examples of antiinflammatory substances are beclomethasone, budesonide, dexamethasone, flunisolide, fluticasone, tipredane and triamcinolone; examples of antitussives are narcotine and noscapine; examples of bronchodilators are bambuterol, bitolterol, carbuterol, clenbuterol, ephedrine, epinephrine formoterol, fenoterol, hexoprenaline, ibuterol, isoprenaline, isoproterenol, metaproterenol, orciprenaline, phenylephrine, phenylpropanolamine, pirbuterol, procaterol, reproterol, rimiterol, salbutamol, salmeterol, sulfonterol, terbutalin and tolobuterol; examples of diuretics are amiloride and furosemide; an example of enzymes is trypsin; examples of cardiovascular substances are diltiazem and nitroglycerine; examples of hormones are cortisone, hydrocortisone and prednisolone; examples of proteins and peptides are cyclosporins, cetrorelix, glucagon and insulin. Other active compounds which can be employed are adrenochrome, colchicine, heparin, scopolamine. The active compounds mentioned by way of example can be employed as free bases or acids or as pharmaceutically tolerable salts. Counterions which can be employed are, for example, physiologically tolerable alkaline earth metals or alkali metals or amines, as well as, for example, acetate, benzenesulfonate, benzoate, hydrogen carbonate, hydrogen tartrate, bromide, chloride, iodide, carbonate, citrate, fumarate, malate, maleate, gluconate, lactate, pamoate and sulfate. Esters can also be employed, for example acetate, acetonide, propionate, dipropionate, valerate.

The formulation according to the invention can also consist of a mixture of several finely ground active compounds, for example of sodium cromoglycate and reproterol hydrochloride. As already described, 100% of the active compound particles should be less than 10 μm, preferably in the range from 1 μm to 5 μm.

The excipient employed is a nontoxic material which has a mean particle size of 200 μm to 1000 μm, preferably between 300 μm and 600 μm. Excipients according to the invention inorganic salts such as sodium chloride and calcium carbonate, organic salts such as, for example, sodium lactate and organic compounds such as, for example, urea, monosaccharides such as, for example, glucose and its derivatives such as sorbitol, polyalchohols, sorbitol, mannitol, xylitol, disaccharides such as, for example, lactose, maltose and their derivatives, and polysaccharides such as, for example, starch and its derivatives, oligosaccharides such as, for example, cyclodextrins, and also dextrins can be employed. Mixtures of the auxiliaries can also be employed.

The ratio of active compound to the excipient material depends on the substances employed. By means of the examples, it has been shown that the use of 10 to 80 percent by weight of the active compound to 20 to 90 percent by weight of the excipient, preferably 30 to 70 percent by weight of the active compound to 30 to 70 percent by weight of the excipient, gives satisfactory results.

Additionally to the active compound and excipient, the formulations can also contain other constituents, such as flavor corrigents, for example saccharin or peppermint flavoring. The components can be, for example, 10–20% by weight relative to the active compound or to the active compound mixture.

The preparation of the formulation is carried out by mixing the constituents in a suitable mixer, for example tumble mixer, rotary mixer, high-speed mixer or fluidizing mixer. A possible tumble mixer is, for example, the Turbula mixer, W. A. Bachofen AG, Basle, CH; a high-speed mixer is the Diosna mixer, Dierks und Söhne, Osnabrück, FRG.

The constituents here are added to the mixer and mixed until the excipient crystals are coated with the fine active compound or active compound mixture, the fine fraction gradually disappearing and round, coated particles resulting.

However, other processes such as fluidized bed or vibration processes can also be used for the preparation of the powder formulations according to the invention. In these processes, the excipient particles are set into rotary motion in a container. The active compound particles are thereby able to deposit thereon and thus form the formulation according to the invention.

In order to demonstrate the advantages of the formulation according to the invention in comparison to the mixture of the two active compounds and the soft pellets according to specifications GB 1,569,612 and GB 1,520,247, these formulations were prepared and some physical measurements were determined.

DETAILED DESCRIPTION OF THE INVENTION

The preparation of the mixture of the two active compounds was carried out with the aid of a tumble mixer (Turbula mixer; W. A. Bachofen AG Basle). The soft pellets were prepared by transferring the fine active compounds to the bottom container of a sieve tower for particle size analysis (Retsch, FRG), and the container was exposed to vibrations until round active compound agglomerates resulted.

The following tables show some comparative measurement results.

EXPERIMENT 1

Active Compound Mixture:

Two parts by weight of disodium cromoglycate and one part by weight of reproterol hydrochloride.

|  | Core agglomerates | Mixture | Soft pellets |
|---|---|---|---|
| Bulk volume (ml/g) | 2.2 | 7.2 | 3.8 |
| Compacted volume (20x) (ml/g) | 2 | 5 | 3 |
| Hausner factor | 1,10 | 1,44 | 1,27 |
| Bed height (mm) | 24 | 35 | 29 |
| Redispersion (%) at 60 l/min/volume flow [sic] | 50 | 40 | 35 |
| Redispersion (%) at 30 l/min/volume flow [sic] | 30 | 10 | 15 |

The soft pellets were obtained according to the procedures of GB 1,569,612 and GB 1,520,247.

EXPERIMENT 2

Active Compound Mixture:

Three parts by weight of disodium cromoglycate and two parts by weight of reproterol hydrochloride.

|  | Core agglomerates | Mixture | Soft pellets |
|---|---|---|---|
| Bulk volume (ml/g) | 2 | 7.2 | 3.8 |
| Compacted volume (20x) (ml/g) | 1.9 | 5 | 3 |
| Hausner factor | 1,05 | 1,44 | 1,27 |
| Bed height (mm) | 23 | 35 | 29 |
| Flow angle (°) | 48 | 59 | 54 |

Bulk volume and compacted volume were determined according to known processes.

100 g of formulation are carefully tipped into a measuring cylinder. The volume read off represents the bulk volume. The filled measuring cylinder is attached to a compacted volume meter. 20 compactions are carried out. The volume read off represents the compacted volume (see also Voigt R., Lehrbuch der pharmazeutischen Technologie [Textbook of Pharmaceutical Technology], Verlag Chemie, 5th Edition, page 148).

The Hausner factor is the ratio of bulk volume to compacted volume.

The bed height was determined with the aid of a cylinder of diameter 42 mm, powder slowly being tipped in until a heap of maximum height resulted, whose height was measured. Redispersion was determined with the aid of an inhaler and of a cascade impactor, by determining the contents in percent based on the initial weight which had been deposited on the second to fourth cascade. This experiment was carried out using two different volume flows.

EXAMPLE 1

266.8 g of micronized disodium cromoglycate and 133.2 g of micronized reproterol hydrochloride are sieved through a sieve of mesh width 0.125 mm and then added to a Diosna mixer PWC Dierks und Söhne, Osnabrück FRG). 600.0 g of commercially available lactose having a grain size distribution of 100%<800 µm, 12%–35%<400 µm and max 7%<200 µm are added thereto. Mixing is then carried out for 30 min. The core agglomerates thus resulting are readily flowable and can be filled into an inhaler. The properties of these core agglomerates can be seen from Experiment 1 (page 8).

EXAMPLE 2

3000 g of micronized disodium cromoglycate and 200.0 g of micronized reproterol hydrochloride are sieved through a sieve of mesh width 0.125 mm and then added to a tumble mixer (Turbula mixer; W. A. Bachofen AG Basle). 500.0 g of commercially available lactose having a grain size distribution of 100%<800 µm, 12%–35%<400 µm and max 7%<200 µm are added thereto. Mixing is then carried out for 30 min. The core agglomerates thus resulting are readily flowable and can be filled into an inhaler. The properties of these core agglomerates can be seen from Experiment 2 (page 9).

EXAMPLE 3

266.8 g of micronized disodium cromoglycate and 133.2 g of micronized reproterol hydrochloride are sieved with the aid of a 0.125 mm sieve and then added to a fluidizing mixer (Fukae Powtec Corporation, Japan).

600.0 g of commercially available sodium chloride having an average grain size of 300 µm are added thereto. Mixing is then carried out for 10 min. The core agglomerates thus resulting are readily flowable and can be filled into an inhaler.

EXAMPLE 4

30 g of micronized budesonide are sieved with the aid of a 0.125 mm sieve and then added to a tumble mixer (Tubula mixer; W. A. Bachofen [sic] AG, Basle). 270 g of commercially available lactose having a grain size distribution of 100%<800 µm, 12%–35%<400 µm and at most 7%<200 µm are added thereto. Mixing is then carried out for 45 min. The core agglomerates thus resulting are readily flowable and can be filled into an inhaler, a cartridge or blister packs.

EXAMPLE 5

100 g of micronized salbutanol are sieved with the aid of a 0.125 mm sieve and then added to a tumble mixer (Tubula mixer; W. A. Bachofen AG, Basle). 300 g of commercially available lactose having a grain size distribution of 100%<800 µm, 12%–35%<400 µm and at most 7%<200 µm are added thereto. Mixing is then carried out for 45 min. The core agglomerates thus resulting are readily flowable and can be filled into an inhaler, a cartridge or blister packs.

EXAMPLE 6

20 g of micronized hecclometasone-17,21-dipropionate are sieved with the aid of a 0.125 mm sieve and then added to a tumble mixer (Turbula mixer; W. A. Bachofen AG, Basle). 380 g of commercially available lactose having a grain size distribution of 100%<800 µm, 12%–35%<400 µm and at most 7%<200 µm are added thereto. Mixing is then carried out for 45 min. The core agglomerates resulting in this way are readily flowable and can be filled into an inhaler, a cartridge or blister packs.

EXAMPLE 7

20 g of micronized ipratropium bromide are sieved with the aid of a 0.125 µm sieve and then added to a tumble mixer (Turbula mixer; W. A. Bachofen AG, Basle). 380 g of commercially available lactose having a grain size distribution of 100%<800 μm, 12%–35%<400 μm and at most 7%<200 μm are added thereto. Mixing is then carried out for 45 min. The core agglomerates resulting in this way are readily flowable and can be filled into an inhaler, a cartridge or blister packs.

What is claimed is:

1. A formulation comprising an active compound mixture having a mean particle size of 0.1 μm to 10 μm in combination with a physiologically acceptable excipient or excipient mixture having a mean particle size of 400 μm to 1000 μm and a rugosity greater than 1.75.

2. A formulation comprising an active compound mixture having a mean particle size of 1 μm to 5 μm in combination with a physiologically acceptable excipient or excipient mixture having a mean particle size of 400 μm to 600 μm and a rugosity greater than 1.75.

3. A process for the preparation of a formulation for production of medicaments for inhalation, comprising mixing an active compound or an active compound mixture having a mean particle size of 0.1 μm to 10 μm with a physiologically acceptable excipient or excipient mixture having a mean particle size of 400 μm to 1000 μm and a rugosity greater than 1.75.

4. The process according to claim 3 wherein the active compound or active compound mixture has a mean particle size of 1 μm to 5 μm and the physiologically acceptable excipient or excipient mixture has a mean particle size of 400 μm to 600 μm.

5. The process according to claim 3 or 4 wherein the excipient particles are covered by the active compound particles.

6. The formulation according to claim 1 or 2 wherein the active compound or an active compound mixture is present in an amount between 5 and 80% by weight and the excipient or excipient mixture is present in an amount between 20 and 95% by weight.

7. The formulation according to claim 6 wherein the active compound or an active compound mixture is present in an amount between 30 and 70% and the excipient or excipient mixture is present in an amount between 30 and 70%.

8. The formulation according to claim 1 or 2 additionally comprising further physiologically acceptable auxiliaries.

9. The formulation according to claim 1 or 2 wherein the excipient contains at least one substance from the saccharides group.

10. The formulation according to claim 1 or 2 wherein the excipient contains lactose.

11. The formulation according to claim 1 or 2 wherein the active compound mixture is a mixture of reproterol and the disodium salt of cromoglycic acid.

12. The formulation according to claim 1 or 2 wherein the active compound is budesonide.

13. The formulation according to claim 1 or 2 wherein the active compound is salbutamol.

14. The formulation according to claim 1 or 2 wherein the active compound is cetrorelex.

15. The formulation according to claim 1 or 2 wherein the active compound is beclometasone.

16. The formulation according to claim 1 or 2 wherein the active compound is ipratropium bromide.

* * * * *